United States Patent [19]
Fishman

[11] Patent Number: 6,066,856
[45] Date of Patent: May 23, 2000

[54] RADIATION PROTECTIVE DEVICE

[75] Inventor: Steven J. Fishman, Weston, Mass.

[73] Assignee: Children's Medical Center Corporation, Boston, Mass.

[21] Appl. No.: 09/080,447

[22] Filed: May 18, 1998

[51] Int. Cl.$^7$ ............................................. G21F 1/00
[52] U.S. Cl. ................................ 250/519.1; 250/516.1; 250/515.1; 623/8; 623/12; 623/66
[58] Field of Search .......................... 250/519.1, 516.1, 250/515.1; 623/8, 11, 12, 66

[56] References Cited

U.S. PATENT DOCUMENTS

| | | | |
|---|---|---|---|
| 2,959,166 | 11/1960 | Clayton . | |
| 3,872,856 | 3/1975 | Clayton | 128/1.2 |
| 4,190,040 | 2/1980 | Schulte | 128/1 R |
| 4,190,046 | 2/1980 | Virag | 128/200.21 |
| 4,217,889 | 8/1980 | Radovan et al. | 128/1 R |
| 4,223,229 | 9/1980 | Persico et al. | 250/515 |
| 4,543,008 | 9/1985 | Salama et al. | 403/174 |
| 4,558,093 | 12/1985 | Hatzenbuhler et al. | 524/837 |
| 4,666,447 | 5/1987 | Smith et al. | 623/8 |
| 5,148,040 | 9/1992 | Wise, Jr. et al. | 250/515.1 |
| 5,344,459 | 9/1994 | Swartz | 623/18 |
| 5,375,612 | 12/1994 | Cottenceau et al. | 128/899 |
| 5,496,370 | 3/1996 | Hamas | 623/11 |
| 5,550,383 | 8/1996 | Haskell | 250/519.1 |
| 5,558,829 | 9/1996 | Petrick | 264/263 |
| 5,571,179 | 11/1996 | Manders et al. | 623/8 |
| 5,577,368 | 11/1996 | Hamilton et al. | 53/432 |
| 5,578,079 | 11/1996 | Kamel et al. | 623/6 |
| 5,605,530 | 2/1997 | Fischell et al. | 600/3 |

FOREIGN PATENT DOCUMENTS

| | | | |
|---|---|---|---|
| 2151927 | 7/1985 | United Kingdom | A61F 2/00 |

*Primary Examiner*—Teresa Arroyo
*Assistant Examiner*—Nikita Wells
*Attorney, Agent, or Firm*—Nutter, McClennen & Fish, LLP

[57] ABSTRACT

The present invention is a bioimplantable device for adjusting the position of and/or shielding selected tissues of a human body during radiation therapy. The device includes a selectively inflatable hollow structure formed from a biocompatible material, an inflation port in communication with the hollow structure effective to communicate an inflation material to within the hollow structure and at least one tissue fixation element disposed on the hollow structure.

In another embodiment, the device is a multi-layer structure which can be implanted to block radiation and/or displace tissues from the path of the radiation.

29 Claims, 5 Drawing Sheets

6,066,856

RADIATION PROTECTIVE DEVICE

CROSS-REFERENCE TO RELATED APPLICATIONS

Not applicable.

STATEMENTS REGARDING FEDERALLY SPONSORED RESEARCH

Not applicable.

BACKGROUND OF THE INVENTION

Radiation therapy has been the preferred method for treating many kinds of cancer in different parts of the body. In fact, half of all people afflicted with cancer are treated with radiation, and the number of cancer patients who have been cured is rising every day. For many patients, radiation is the only kind of treatment needed. In fact, a large number of people are free of cancer after having radiation treatments alone or in combination with surgery, chemotherapy, or biological therapy.

Doctors can also use radiation before surgery to shrink certain types of tumors. After surgery, radiation therapy may be used to stop the growth of any cancer cells that remain. Even when curing the cancer is not possible, radiation therapy still can bring relief. Many patients find the quality of their lives improved when radiation therapy is used to shrink tumors and reduce pressure, bleeding, pain, or other symptoms of cancer.

Radiation therapy can be in either of two forms: external or internal. Some patients receive both forms of therapy, typically one after the other. Most people who receive radiation therapy for cancer are treated with the external type of radiation therapy which is usually given during outpatient visits to a hospital or treatment center. In external therapy, a machine directs high-energy rays or particles at the cancer and the normal tissue surrounding it. One type of machine that is used for radiation therapy is called a linear accelerator. High-energy rays may also come from a machine that contains radioactive substance such as cobalt-60. The various machines used for external radiation work in slightly different ways and some are better for treating cancers near the skin surface while others work best on cancers deeper in the body.

However, like many other treatments for disease, there are risks for patients who are receiving radiation therapy. The brief high doses of radiation that damage or destroy cancer cells also can affect normal cells. When this happens, the patient has side effects which can be manifested in the form of headaches, loss of appetite, loss of hair, lethargy, etc. In fact, high doses of radiation can actually kill cells or keep them from growing and dividing. Furthermore, the function of organs near a cancer can be impaired by the radiation. This risk often limits the utility of radiation therapy. Ideally, radiation could be delivered to the area or organ of interest with little or no exposure to normal adjacent tissues.

The conventional method of protecting healthy areas or cells from exposure to the radiation treatment involves the use of external blocking shields or pads which are used to cover certain parts of the body to protect normal tissues and organs. Unfortunately, due to the basic overlapping nature of tissues and organs within the human body, these prior art devices for preventing irradiation of normal tissues are limited in their effectiveness. Furthermore, it is often difficult to concentrate the radiation in an easily definable area. As a result, areas surrounding the site to be irradiated are more often than not exposed to the radiation.

Thereby it would be desirable to have a device for more effectively and predictably controlling the exposure of the human body parts to radiation during radiation therapy. Such a device would either shield the tissues to be protected from radiation or displace them from the tissues to be irradiated such that a highly effective dose of energy could be delivered to the malignancy and little or none delivered to the surrounding or adjacent tissues or organs.

BRIEF SUMMARY OF THE INVENTION

The present invention is a bioimplantable device for adjusting the position of and/or shielding selected areas of a human body during radiation therapy. The device includes a selectively inflatable hollow structure formed from a biocompatible material, an inflation port in communication with the hollow structure effective to communicate an inflation material to within the hollow structure and at least one tissue fixation element disposed on the hollow structure.

In another embodiment, the device would be pre-inflated to a fixed volume before implantation. In this embodiment, an inflation port would be optional.

In yet another embodiment, the device is a multi-layer bioimplantible structure for implantation into a site to be irradiated. The structure also includes al least one tissue fixation element disposed on the structure.

BRIEF DESCRIPTION OF THE DRAWINGS

The foregoing features of this invention, as well as the invention itself, may be more fully understood from the following description of the drawings in which.

DETAILED DESCRIPTION OF THE INVENTION

Figure 1:
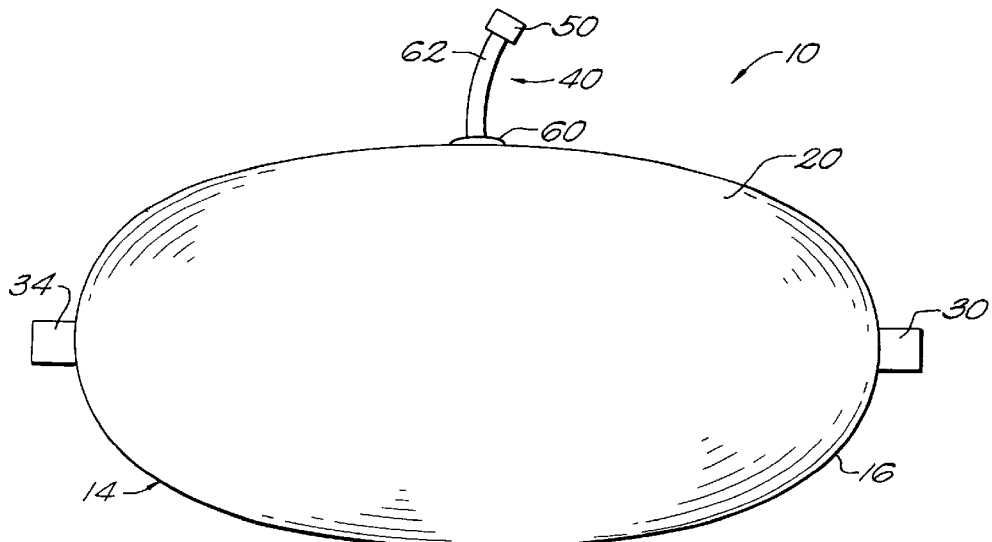
FIG. 1 illustrates an implantable radiation protective device according to the present invention.

The present invention provides a radiation protective device for the selective displacement and/or shielding of selected areas of a human body during radiation therapy treatment. Referring to FIG. 1, an exemplary embodiment of the device 10 includes a hollow bladder structure 20, tissue fixation elements 30, 32 and 34 and an access port assembly 40.

Figure 2:
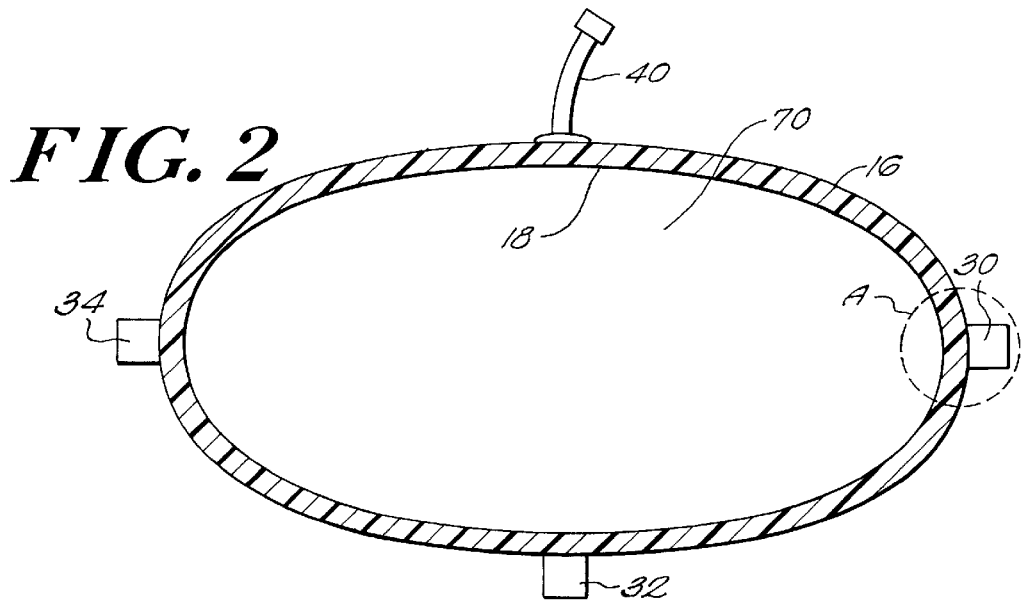
FIG. 2 is a sectional view of the inflatable radiation protective device of FIG. 1.

In an exemplary embodiment, the bladder 20 is defined by a substantially oval-like outer surface 14. As shown in FIG. 2, the bladder 20 is further includes an inner bladder surface 18 which defines an internal chamber 70. The bladder 20 can be made of a biocompatible high-density material such as silicone rubber, polyethylene, or any other material suitable for implantation as is known by those skilled in the art. In other embodiments, the bladder 20 can be made of a bioabsorbable material such as polylactide polymer, polyglycolic acid, and polycaprolactone, to remain in the tissue to be absorbed therein.

One of ordinary skill in the art will readily appreciate that the bladder can be configured in a variety of additional shapes and materials depending on a number of factors, including the site of implantation, method of implantation and/or type of radiation to be used. The size of the bladder will vary according to the specific implantation site and the level of inflation applied to each bladder.

Connected to the outer surface 14 of the bladder 20 along a peripheral edge 16 is the access port assembly 40. The access port assembly 40 is adapted for communication with a needle or catheter, not shown, where it is desired to infuse or withdraw from the bladder gas or fluid. In an exemplary embodiment, the fluid can be water, saline and/or a radio-opaque agent. As used herein, the term radio-opaque encompasses any material and/or fluid with properties which tend to block, absorb and/or disperse radiation. The term radiotransparent as used herein means any material which allows the passage of radiation. The access port assembly 40 includes a base portion 60, a connector tube 62 and a sealing cap or dome 50. In other embodiments, the access port assembly may include just the base portion 60 and the sealing cap or dome 50.

The sealing cap 50 is adapted to allow for either the withdrawal or injection of fluid, gas and/or radio-opaque material. The sealing cap 50 further acts as a septum to prevent body fluids from entering the radiation protective device 10. In an exemplary embodiment, the sealing cap 50 is made of an elastomeric material such as silicone rubber or the like, that it is capable of self-sealing around an introducer needle (not shown). The sealing cap 50 should be of sufficient diameter to allow passage of a needle or other elongate medical instrument therethrough.

In one embodiment the sealing cap 50 is subcutaneously implanted and access to the device, to infuse or remove material through the access port, is accomplished using a hypodermic needle or catheter type device. Alternatively, a portion of the connection tubing 62 and the sealing cap 50 may be exposed outside of the body and access to the sealing cap 50 is effected without penetrating the patient's body.

In alternate embodiments, the cap includes a sealing valve, not shown, which is a "duck-bill" type valve. Examples of such valves include, but are not limited to, a movable diaphragm and multiple leaf valve.

Figure 3:
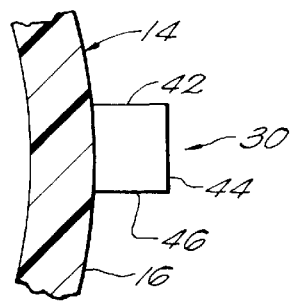
FIG. 3 is a detailed view of portion A in FIG. 2.

Referring to FIG. 3, one embodiment of a tissue fixation element 30 is shown in greater detail. The tissue fixation element 30 includes opposed walls 42, 46, which are joined by an end wall portion 44. The tissue fixation element can be separately attached to the bladder 20 by sewing or otherwise affixing a separate flap or appendage to the bladder. In other embodiments, tissue fixation element 30 can be molded integrally with the peripheral edge 16 of the bladder 20. Although the illustrated embodiment shows a radiation protective device with three tissue fixation elements, it is understood that the device may have one, two or more than three tissue fixation elements. Additionally, the tissue fixation elements may be arranged in any number of fashions in relation to one another. In a further embodiment of the tissue fixation element, the element is a continuous flap of material, not shown, which extends entirely around the periphery of the bladder and allows attachment along any point of the periphery. The tissue fixation elements are preferably made of a biocompatible material similar to the construction of the bladder.

As discussed below, the device 10 can be secured within the body by a variety of techniques. Regardless of how device 10 is secured, it should be securely implanted so that it is not dislodged as a result of patient movement.

In an exemplary embodiment, the tissue fixation elements are adapted for standard suture connection to secure the device 10 to human tissue, organs, and/or bone. Sutures for closing incisions or wounds are well known in the prior art. Such sutures are available in a wide variety of materials including monofilament, braided material, cat gut, silk, nylon, polyester, polyolefins such as polypropylene, linen, cotton as well as bioabsorbable materials, such as polyglactin. One of ordinary skill in the art will appreciate that the device 10 may be secured by sutures using any known suturing technique. Such techniques include suturing during conventional, open surgery as well as during minimally invasive surgical techniques including laparoscopy, thoracoscopy, arthroscopy, endoscopy (gastrointestinal, airway, sinus, genitourinary), ventriculoscopy and soft tissue endoscopy.

Alternatively, the tissue fixation element as shown and described herein may be adapted for use with surgical fasteners or staples to attach to body tissue either through open or minimally invasive surgical procedures.

The tissue fixation element can also be adapted for attachment of the radiation protective device directly to bone, using devices such as screws, staples, cement, suture anchors, and sutures.

Figure 4:
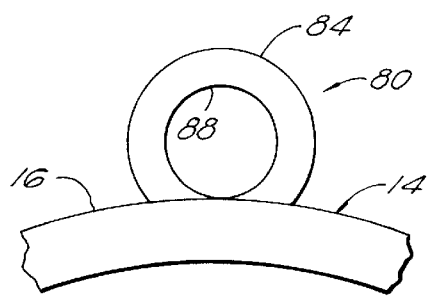
FIG. 4 is another embodiment of the tissue fixation element.

In another embodiment, as shown in FIG. 4, the tissue fixation element is a substantially loop-like structure 80, defined by an outer loop wall 84 and an inner loop wall 88. As discussed above, a number of different fixation methods such as suturing and stapling can be employed to fasten the tissue fixation element 80 to tissue, organs, and/or bone.

Figure 5:
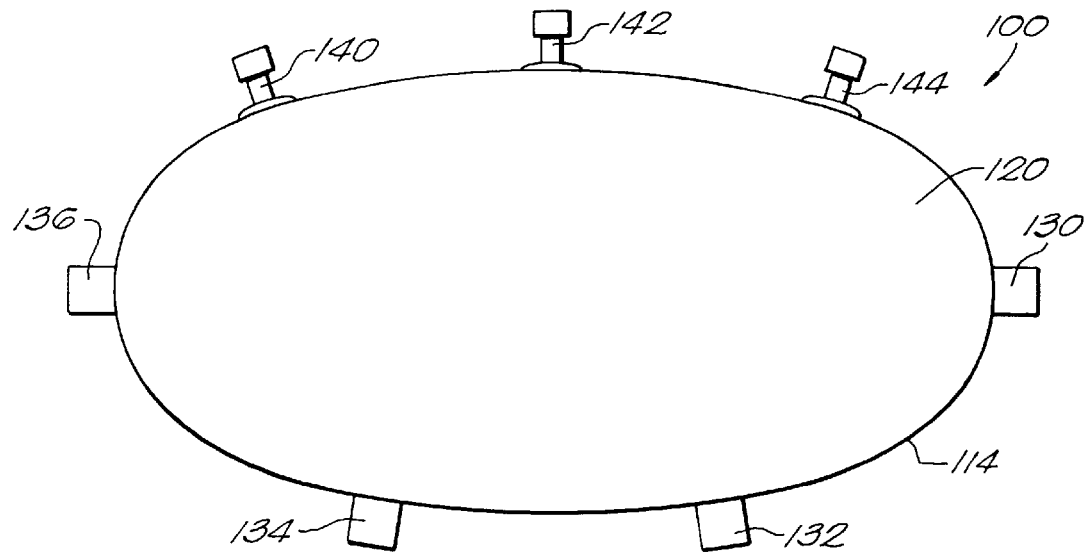
FIG. 5 illustrates another embodiment of the device having multiple inflatable compartments.
Figure 6:
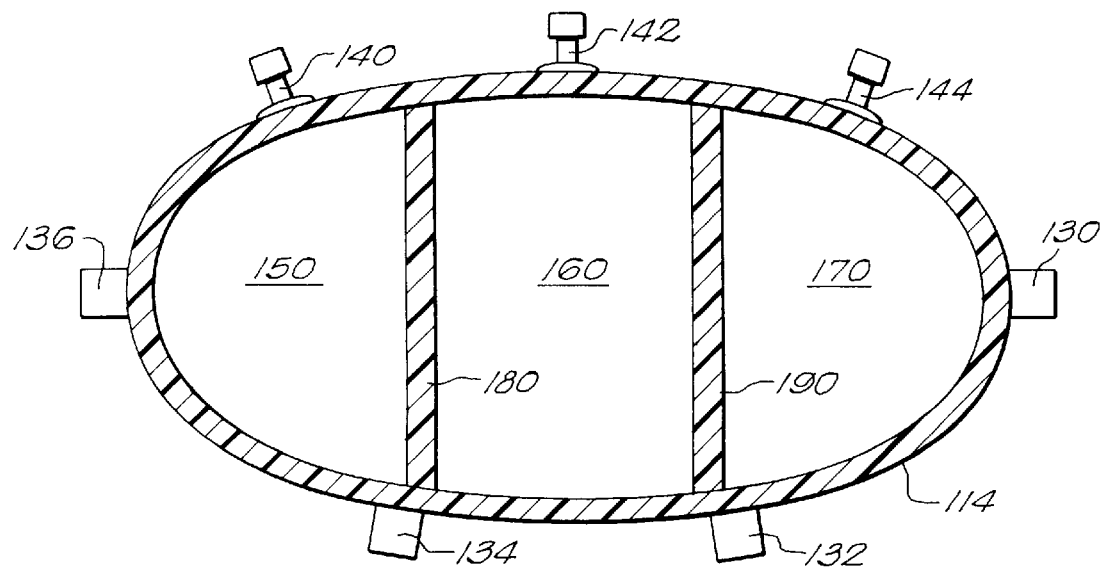
FIG. 6 is a sectional view of the device of FIG. 5.

FIGS. 5 and 6 illustrate another embodiment in which the radiation protective device 100 includes a plurality of separately inflatable compartments 150, 160 and 170 enclosed within a unitary bladder 120. The device 100 further includes access port assemblies 140, 142 and 144 and tissue fixation elements 130, 132, 134 and 136. Although the illustrated embodiment shows the bladder with three compartments, other embodiments of the device may have two compartments or more than three compartments. Additionally, each compartment may be arranged in any number of fashions in relation to one another. For example, instead of having the compartments in a linear sequential fashion as illustrated, the compartments may form an "L" shape or any other shape which is desired.

As shown in FIG. 6, each compartment may be independently inflated and deflated via dedicated inflation access port assemblies 140, 142 and 144. In other variations of the embodiment shown in FIG. 6, the multiple port assemblies can be brought together and accessed through a singular unified housing with multiple injection wells. The compartments may be filled with a liquid, a gas or a combination of both. The compartments may also be selectively inflated and/or deflated depending on the desired shape of the device. For example, compartments 150 and 170 may be fully inflated with compartment 160 being only partially inflated thereby imparting a "dog-bone" like shape to the bladder 120. It is further contemplated that one or more of the inflatable compartment or compartments may come pre-inflated with either a gas, or a fluid such as saline or a radio-opaque material, rather than being inflated after implantation in the body. In such an embodiment, the remaining compartments which have not been pre-inflated may be selectively inflated to achieve the desired shape to the device.

Figure 7:
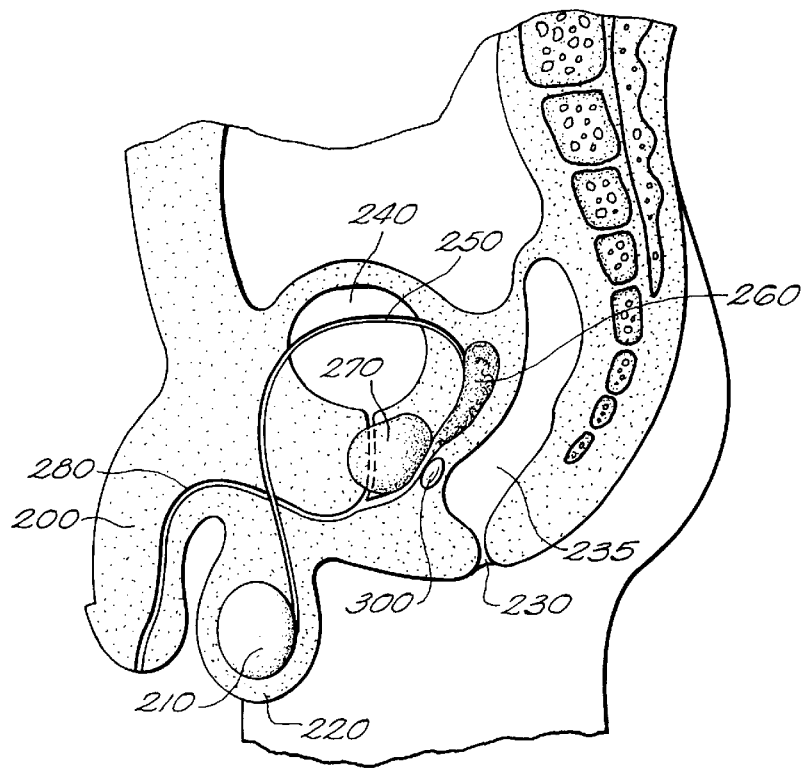
FIG. 7 is a side view of the inflatable radiation protective device disposed between the male prostate and rectum.
Figure 8:
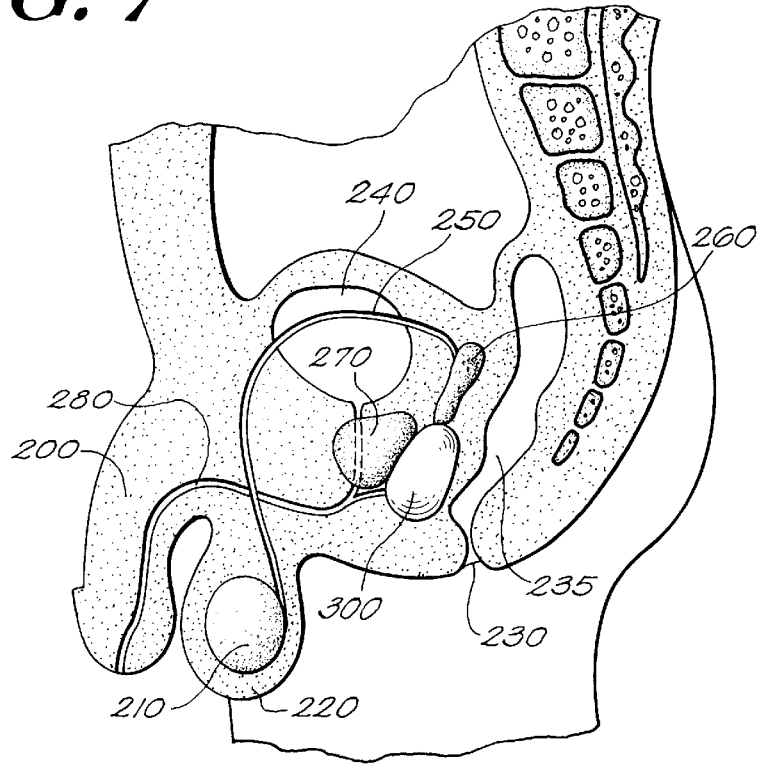
FIG. 8 is a side view of the radiation protective device of FIG. 7 in an inflated condition.

Turning now to FIGS. 7 and 8, an exemplary use of the radiation adjustment device is illustrated with respect to an external beam irradiation procedure for the male prostate. During conventional irradiation of the prostate, serious side effects may occur due to the resultant irradiation of areas of healthy tissue surrounding the prostate. These side effects may include diarrhea, intestinal discomfort, incontinence, fatigue, and impotence.

As shown in FIG. 7, the human male pelvic anatomy includes a penis 200, testicles 210, scrotum 220, anus 230 and rectum 235. The urinary bladder 240 is connected to the penis 200 by the urethra 280. The testicles 220 convey sperm through the was deferens 250 and join seminal fluid from the seminal vesicles 260 which passes through the prostate 270 into the urethra 280. The prostate 270 sits below the urinary bladder 240, anterior and adjacent to the rectum 235.

Once the patient has been prepared for surgery, a radiation protection device 300 is inserted into the body between the prostate 270 and rectum 235. The device 300 may be secured in place by sutures or other means. The surgeon then seals the incision, leaving the access tube protruding from the body or under the skin in a location accessible for needle or other similar implement insertion. Alternatively, the device 300 may be placed through minimally invasive techniques as described above.

As demonstrated in FIG. 8, the device 300 is then inflated to displace the rectum 235 from the prostate 270. The external beam radiation treatment can then proceed with the rectum 235 either being displaced from the path of the radiation (e.g. in the case of a lateral incident beam), sufficiently separated from the prostate such that the incident radiation cannot significantly penetrate to the depth of the rectum or shielded by material within the device 300 which reduces the penetration of or is impervious to the radiation (e.g. in the case of an anterior incident beam). The device 300 may be inflated with a gas or a fluid. One exemplary inflation fluid is a radio-opaque fluid, such as liquid mercury, which can provide additional shielding protection. The device 300 is left in place during the treatment process, which may extend over several days or weeks. After treatment, the device may be removed or, if constructed of bioabsorbable material, left in place to degrade over time.

The device as described herein can be used for a variety treatments aside from the prostate application as previously discussed. For example, the device can be configured in a variety of shapes and sizes to be used in any anatomic location including the thoracic cavity, mediastinum, abdomen, pelvis, soft tissues of the head, neck, torso, extremities, genitalia or any other body site or organ. In applications in which prolonged inflation of the device might cause physiologic disturbance, the radiation therapy can be administered in altered fractions so that the device can be intermittently inflated and deflated. Preferably, the radiation is administered only when the device is in the inflated condition.

Figure 9:
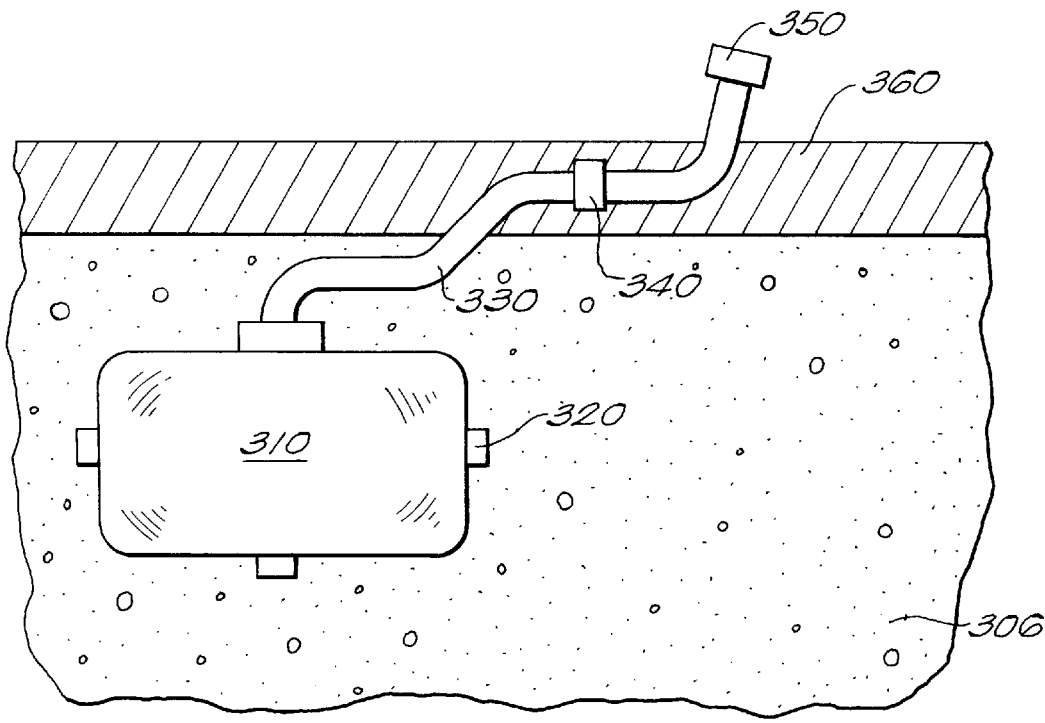
FIG. 9 is an illustration of an embodiment of the radiation protection device utilizing a protective grommet.

Another exemplary implantation of the radiation protective device is shown in FIG. 9. As shown, an inflatable bladder 310 having a plurality of fixation elements 320 is implanted in the body 306. The bladder includes a connector tube 330 which is externally accessed through port 350. A grommet 340 may be used to assist in securing the connector tube 330 to the body and to encourage ingrowth of subcutaneous tissue to minimize infection. The grommet 340 is sized and shaped to be attached around the connector tube 330 at a point along the length of the connector tube 330. Once implanted, the grommet 340 becomes entrenched in the subcutaneous tissue 360 and helps secure the connector tube 330 from inadvertently being removed.

Figure 10:
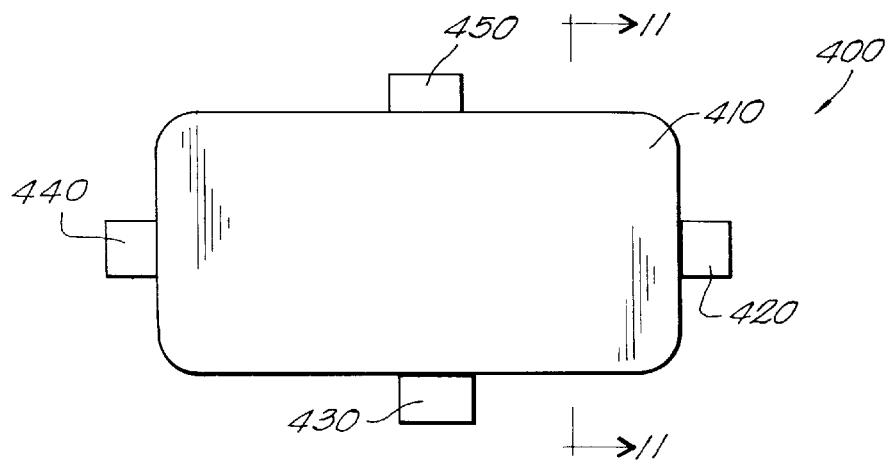
FIG. 10 is a top view of another embodiment of the radiation protective device.

FIG. 10 illustrates an exemplary embodiment in which a radiation protective device 400 includes a flexible body portion 410 and tissue fixation elements 420, 430, 440 and 450. Preferably, the substantially rectangular body portion 410 is made of a biocompatible, fluid and gas impermeable material which can be constructed in a variety of shapes and configurations. Additionally, the body portion may include a radio-opaque material to provide for radiation shielding once the device is implanted within the human body.

Figure 11:
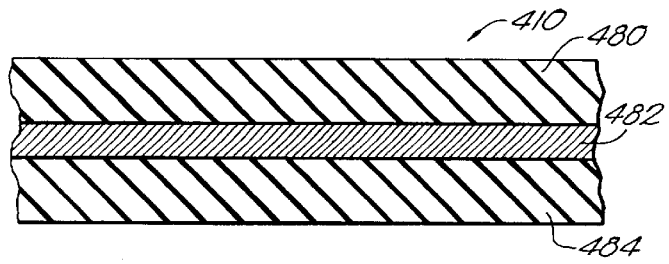
FIG. 11 is a view along line 11—11 in FIG. 10.

In an exemplary embodiment, the body portion 410 has a multi-layer construction, as shown in FIG. 11. The body portion 410 includes a first layer 480 of flexible and pliable material such as rubber. Interposed is a second layer 482 of radio-opaque material such as lead or other similar radio-opaque material as is known to those skilled in the art. A third layer of rubber 484 encloses the second layer 482 and thereby forms the multi-layer construction. It will also be known to those of ordinary skill in the art that the body portion may be configured in a variety of shapes and sizes, suitable to the area of implantation.

Figure 12:
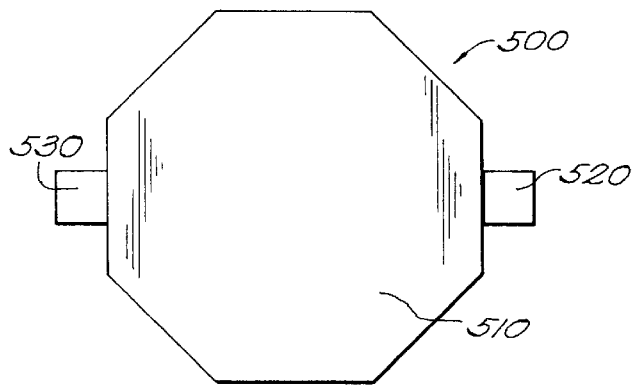
FIG. 12 is a top view of another embodiment of the radiation protective device.
Figure 13:
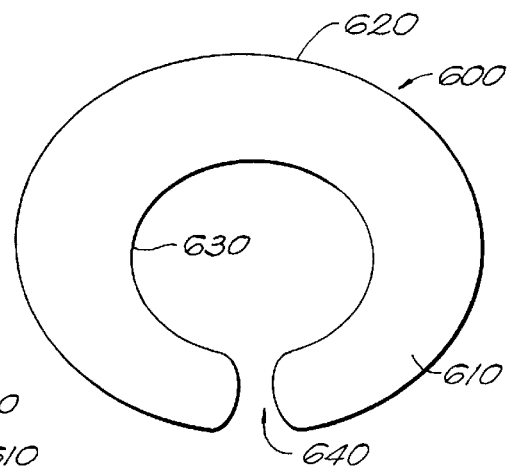
FIG. 13 is a top view of yet another embodiment of the radiation protective device.
Figure 14:
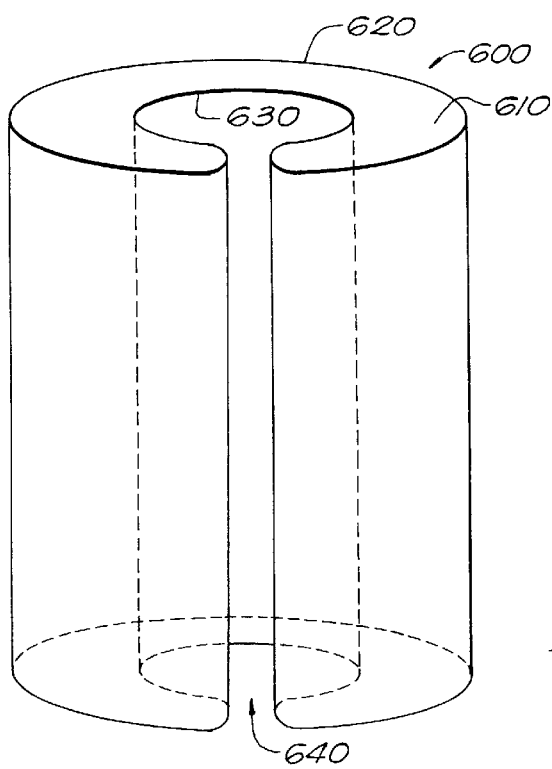
FIG. 14 is a perspective view of the embodiment of the radiation protective device shown in FIG. 13.

Further embodiments of the radiation protective device structure are shown in FIGS. 12 and 13. As shown in FIG. 12, a radiation protective structure 500 includes a body portion 510 with tissue fixation elements 520 and 530. As shown in FIG. 13, a radiation protective structure 600 includes a substantially donut-like shaped body portion 610 which may be useful for implantation around a tubular organ such as the esophagus. The structure 600 further includes an outer wall surface 620 and an inner wall surface 630. The structure 600 may be non-contiguous and may include gap or notch 640 in the structure 600 to allow for ease of implantation. The structure could be configured in a variety of heights, such as illustrated in FIG. 14 to conform to a tubular organ such as the esophagus. Like other embodiments of the invention, the structures shown in FIGS. 12, 13 and 14 can be configured as a solid structure, or they can be in the form of a hollow bladder to allow for selective inflation and/or deflation.

Having described the preferred embodiments of the invention, it will now become apparent to one of ordinary skill in the art that other embodiments incorporating their concepts may be used. For example, the embodiments as shown in FIGS. 1 and 10 may be combined into a device having one inflatable section and one non-inflatable solid section. These embodiments should not be limited to disclosed embodiments, but rather should be limited only by the spirit and scope of the appended claims. All publications and references cited herein are expressly incorporated herein by reference in their entirety.

What is claimed is:

1. A bioimplantable device, comprising:
    a selectively inflatable hollow structure formed from a biocompatible material;
    an inflation port in communication with the hollow structure effective to communicate an inflation material to within the hollow structure; and at least one tissue fixation element disposed on the hollow structure.

2. The bioimplantable device of claim 1, wherein the structure is effective to shield at least a portion of at least one or more internal organs and surrounding tissue from radiation.

3. The bioimplantable device of claim 1, wherein the structure is effective to support and move organic tissue from a first location within the body to a second location within the body.

4. The bioimplantable device of claim 1, wherein the at least one tissue fixation element is a suture engaging structure.

5. The bioimplantable device of claim 1, wherein the at least one tissue fixation element is a staple engaging structure.

6. The bioimplantable device of claim 1, wherein the at least one tissue fixation element is formed from the biocompatible material.

7. The bioimplantable device of claim 2, wherein the biocompatible material is radio-opaque.

8. The bioimplantable device of claim 2, wherein the inflation material is radio-opaque.

9. The bioimplantable device of claim 1, wherein the inflation material is radiotransparent.

10. The bioimplantable device of claim 1, wherein the inflatable hollow structure is comprised of a plurality of separately inflatable compartments.

11. The bioimplantable device of claim 10, wherein each of the separately inflatable compartments has a separate inflation port.

12. The bioimplantable device of claim 1, wherein the inflation port is accessed percutaneously.

13. The bioimplantable device of claim 1, wherein the inflation port is accessed externally.

14. The bioimplantable device of claim 13, further comprising a protective grommet for securing the device after implantation.

15. The bioimplantable device of claim 1, wherein the device is adapted for minimally invasive implantation.

16. The bioimplantable device of claim 1, wherein the device is made of a bioabsorbable material.

17. A bioimplantable structure, comprising:
a body portion, the body portion formed from a biocompatible, fluid and gas impermeable material; and
at least one tissue fixation element disposed on the body portion.

18. The bioimplantable structure of claim 17, wherein the structure is effective to shield at least a portion of at least one or more internal organs and surrounding tissue from radiation.

19. The bioimplantable structure of claim 17, wherein the structure is effective to support and move organic tissue from a first location within the body to a second location within the body.

20. The bioimplantable structure of claim 17, wherein the biocompatible, fluid and gas impermeable material is radio-opaque.

21. The bioimplantable structure of claim 17, wherein the tissue fixation element is a suture engaging structure.

22. The bioimplantable structure of claim 17, wherein the tissue fixation element is a staple engaging structure.

23. The bioimplantable structure claim 17, wherein the structure is adapted for minimally invasive implantation.

24. The bioimplantable structure of claim 17, wherein the tissue fixation element is formed from the biocompatible material.

25. A bioimplantable device, comprising:
a pre-inflated structure formed from a biocompatible material, the structure preinflated with an inflation material; and
at least one tissue fixation element disposed on the structure.

26. The bioimplantable device of claim 25, wherein the structure is effective to shield at least a portion of at least one or more internal organs and surrounding tissue from radiation.

27. The bioimplantable device of claim 25, wherein the structure is effective to support and move organic tissue from a first location within the body to a second location within the body.

28. The bioimplantable device of claim 25, wherein the inflation material is radio-opaque.

29. The bioimplantable device of claim 25, wherein the inflation material is radiotransparent.

* * * * *